United States Patent
Chen

(10) Patent No.: US 7,822,474 B2
(45) Date of Patent: Oct. 26, 2010

(54) METHODS FOR THE PREDICTION OF ARRHYTHMIAS AND PREVENTION OF SUDDEN CARDIAC DEATH

(75) Inventor: Peng-Sheng Chen, La Canada, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 787 days.

(21) Appl. No.: 11/606,636

(22) Filed: Nov. 29, 2006

(65) Prior Publication Data

US 2007/0123945 A1 May 31, 2007

Related U.S. Application Data

(60) Provisional application No. 60/741,172, filed on Nov. 30, 2005.

(51) Int. Cl.
*A61N 1/00* (2006.01)

(52) U.S. Cl. .................. 607/22; 435/7.2; 435/7.92; 530/388; 514/654

(58) Field of Classification Search .............. 530/388; 435/7.2, 7.92; 607/22; 514/654
See application file for complete search history.

(56) References Cited

U.S. PATENT DOCUMENTS

| | | | |
|---|---|---|---|
| 4,026,300 A | 5/1977 | DeLuca et al. | |
| 4,376,110 A | 3/1983 | David et al. | |
| 4,573,481 A | 3/1986 | Bullara | |
| 4,774,967 A | 10/1988 | Zanakis et al. | |
| 4,919,140 A | 4/1990 | Borgens et al. | |
| 5,147,294 A | 9/1992 | Smith et al. | |
| 5,199,428 A | 4/1993 | Obel et al. | |
| 5,203,326 A | 4/1993 | Collins | |
| 5,224,477 A | 7/1993 | Itoh | |
| 5,366,487 A | 11/1994 | Adams et al. | |
| 5,447,520 A | 9/1995 | Spano et al. | |
| 5,471,991 A | 12/1995 | Shinwar | |
| 5,578,061 A | 11/1996 | Stroetmann et al. | |
| 5,658,318 A | 8/1997 | Stroetmann et al. | |
| 5,698,549 A * | 12/1997 | Steers et al. | 514/211.07 |
| 5,700,282 A | 12/1997 | Zabara | |
| 5,921,940 A | 7/1999 | Verrier et al. | |
| 6,272,377 B1 | 8/2001 | Sweeney et al. | |
| 6,308,094 B1 | 10/2001 | Shusterman et al. | |
| 6,351,668 B1 | 2/2002 | Chen | |
| 6,353,757 B2 | 3/2002 | Chen | |
| 6,398,800 B2 | 6/2002 | Chen | |
| 6,516,219 B1 | 2/2003 | Street | |
| 6,521,462 B1 | 2/2003 | Tanouye et al. | |
| 6,593,341 B2 | 7/2003 | Feller et al. | |
| 6,885,888 B2 | 4/2005 | Rezai | |
| 6,950,752 B1 | 9/2005 | Friend et al. | |
| 7,142,911 B2 | 11/2006 | Boileau et al. | |
| 7,257,439 B2 | 8/2007 | Llinas | |
| 7,266,410 B2 | 9/2007 | Chen | |
| 2003/0118652 A1 | 6/2003 | Kelly et al. | |
| 2003/0216349 A1 | 11/2003 | Belardinelli et al. | |
| 2004/0006264 A1 | 1/2004 | Mojarradi et al. | |
| 2004/0014639 A1 | 1/2004 | Belyea et al. | |
| 2004/0054177 A1 | 3/2004 | Otake et al. | |
| 2005/0074821 A1 * | 4/2005 | Wild et al. | 435/7.2 |

FOREIGN PATENT DOCUMENTS

| | | |
|---|---|---|
| EP | 0882452 | 9/1998 |
| WO | WO 99 39624 | 8/1999 |
| WO | PCT/US00/12367 | 5/2000 |
| WO | PCT/AU/00/01362 | 11/2000 |
| WO | PCT/US01/05777 | 2/2001 |
| WO | WO 02 18436 | 3/2002 |

OTHER PUBLICATIONS

Adrian, et al.: Discharges in mammalian sympathetic nerves, *J Physiol* 1932;74:115-133.
Akingba, et al.: Application of nanoelectrodes in recording biopotentials. *Nanotechnology,* 2003. IEEE-NANO 2003;2:870-874.
Akira, et al: Induction of atrial fibrillation and nerve sprouting by prolonged left atrial pacing in dogs. *PACE* 2003;26:2247-2252.
Anthonio et al., "β-Adrenoceptor density in chronic infarcted myocardium: a subtype specific decrease of $β_1$-adrenoceptor density," International Journal of Cardiology, 2000, pp. 137-141, vol. 72, *Elsevier Science Ireland Ltd.,* Ireland.
Antzelevitch, "Tpeak-Tend interval as an index of transmural dispersion of repolarization," *European Journal of Clinical Investigation,* 2001, pp. 555-557, vol. 31, Blackwell *Science* Ltd.
Armour JA: Activity of in situ middle cervical ganglion neurons in dogs, using extracellular recording techniques. *Can.J Physiol Pharmacol.* 1985;63:704-716.
Armour, et al.: Activity of canine in situ left atrial ganglion neurons. *Am.J Physiol* 1990;259:H1207-H1215.
Armour, et al.: Activity of in vivo canine ventricular neurons. *Am.J Physiol* 1990;258:H326-H336.
Arntz, et al.: Circadian variation of sudden cardiac death reflects age-related variability in ventricular fibrillation. *Circulation* 1993;88:2284-89.
Aronow, et al.: Circadian variation of primary cardiac arrest or sudden cardiac death in patients aged 62 to 100 years (mean 82). *Am J Cardiol* 1993;71:1455-1456.
Aronow, et al.: Circadian variation of sudden cardiac death or fatal myocardial infarction is abolished by propranolol in patients with heart disease and complex ventricular arrhythmias. *Am J Cardiol* 1994;74:819-821.
Athill, et al.: Influence of wavefront dynamics on transmembrane potential characteristics during atrial fibrillation. *J Cardiovasc Electrophysiol* 2000; 11:913-921.

(Continued)

*Primary Examiner*—Niketa I Patel
*Assistant Examiner*—Shubatra Narayanaswamy
(74) *Attorney, Agent, or Firm*—Seth D. Levy; Davis Wright Tremaine LLP

(57) ABSTRACT

Methods and kits are provided for determining an increased likelihood of the occurrence of a cardiac arrhythmia, myocardial ischemia, congestive heart failure and other diseased conditions of the heart. The methods and kits comprise measuring serum NGF levels in a subject and detecting increases in NGF levels over baseline. The methods may further comprise initiating preventive therapy in response to a detected increase in serum NGF levels.

19 Claims, No Drawings

OTHER PUBLICATIONS

Barbacid M: Nerve growth factor: a tale of two receptors. *Oncogene* 1993;8:2033-2042.

Barber, et al.: Interruption of sympathetic and vagal-mediated afferent responses by transmural myocardial infarction. *Circulation* 1985;72:623-631.

Barhanin, et al.: KvLQT1 and IsK (minK) proteins associate to form the 1(Ks) cardiac potassium current. *Nature* 1996;384:78-80.

Barrett, et al.: What sets the long-term level of renal sympathetic nerve activity: a role for angiotensin II and baroreflexes? *Circ.Res.* 2003;92:1330-1336.

Bartels et al., "Influence of Myocardial Ischemia and Reperfusion on β-Adrenoceptor Subtype Expression," *Journal of Cardiovascular Pharmacology*, 1998, pp. 484-487, vol. 31, Lippincott-Raven Publishers, Philadelphia, PA, USA.

Bengel, et al.: Myocardial efficiency and sympathetic reinnervation after orthotopic heart transplantation: a noninvasive study with positron emission tomography. *Circulation* 2001;103:1881-1886.

Benjamin, et al.: Impact of atrial fibrillation on the risk of death: the Framingham Heart Study. *Circulation* 1998;98:946-952.

Bers, "Calcium and Cardiac Rhythms: Physiological and Pathophysiological," *Circulation Research*, 2002, pp. 14-17, vol. 90, American Heart Association, USA.

Blakey, et al.: Sudden, unexpected death in cardiac transplant recipients: an autopsy study. *J Heart Lung Transplant* 2001;20:229(abstract).

Boczek-Funcke, et al.: Classification of preganglionic neurones projecting into the cat cervical sympathetic trunk. *J Physiol* 1992;453:319-339.

Bonnemeier, et al.: Course and prognostic implications of QT interval and QT interval variability after primary coronary angioplasty in acute myocardial infarction. *J Am Coll Cardiol* 2001;37:44-50.

Bosch et al., "$β_3$-Adrenergic regulation of an ion channel in the heart-inhibition of the slow delayed rectifier potassium current $I_{Ks}$ in guinea pig ventricular myocytes," *Cardiovascular Research*, 2002, pp. 393-403, vol. 56, Elsevier *Science* B.V.

Bristow et al., "Decreased Catecholamine Sensitivity and β-Adrenergic-Receptor Density in Failing Human Hearts," *The New England Journal of Medicine*, Jul. 22, 1982, pp. 205-211, vol. 307, No. 4, Massachusetts Medical Society, Boston, MA, USA.

Bristow et al., "Reduced $β_1$ Receptor Messenger RNA Abundance in the Failing Human Heart," *The Journal of Clinical Investigation*, Dec. 1993, pp. 2737-2745, vol. 92, The American Society for Clinical Investigation, Inc., USA.

Bristow et al., "$β_1$ and $β_2$-Adrenergic-Receptor Subpopulations in Nonfailing and Failing Human Ventricular Myocardium: Coupling of Both Receptor Subtypes to Muscle Contraction and Selective $β_1$-Receptor Down-Regulation in Heart Failure," *Circulation Research*, Sep. 1986, pp. 297-309, vol. 59, No. 3, American Heart Association, USA.

Bristow et al., $β_1$ and $β_2$-Adrenergic-Receptor-Mediated Adenylate Cyclase Stimulation in Nonfailing and Failing Human Ventricular Myocardium, Molecular Pharmacology, Mar. 1989, pp. 295-303, vol. 35, No. 3, *American Society for Pharmacology and Experimental Therapeutics*, Williams & Wilkins, USA.

Brodde et al., "Adrenergic and Muscarinic Receptors in the Human Heart," Pharmacological Reviews, 1999, pp. 651-689,0031-6997/99/5104-0651, *The American Society for Pharmacology and Experimental Therapeutics*, USA.

Brodde et al., "β-Adrenoceptors in the transplanted human heart: unaltered β-adrenoceptor density, but increased proporation of $β_2$-adrenoceptors with increasing posttransplant time," *Naunyn-Schmiedeberg's Arch. Pharmacol.*, 1991, pp. 430-436, vol. 344, Springer-Verlag.

Brodde et al.: Beta-adrenoceptor density in chronic infarcted myocardium: a subtype specific decrease of betal-adrenoceptor density. *Int J Cardiol* 2000;72:137-41.

Burke, et al.: Evidence for functional sympathetic reinnervation of left ventricle and coronary arteries after orthotopic cardiac transplantation in humans. *Circulation* 1995;91:72-78.

Cao JM, et al.: Nerve sprouting and sudden cardiac death. *Circ Res* 2000 86: 816-821.

Cao JM, et al: Relationship between regional cardiac hyperinnervation and ventricular arrhythmia. *Circulation* 2000; 101:1960-1969.

Centers for Disease Control and Prevention: State-specific mortality from sudden cardiac death—United States, 1999. *MMWR Morb. Mortal.Wkly.Rep.* 2002;51:123-126.

Cesario, et al.: Electrophysiological characterization of cardiac veins in humans. *J Interventional Cardiac Electrophysiol* 2004;10:241-7.

Chang, et al.: Nerve sprouting and sympathetic hyperinnervation in a canine model of atrial fibrillation produced by prolonged right atrial pacing. *Circulation* 2001;103:22-25.

Chaudhry et al., "Differential Interaction of $β_1$- and $β_3$-Adrenergic Receptors with $G_i$ in Rat Adipocytes," *Cellular Signalling*, 1994, pp. 457-465, vol. 6, No. 4, Elsevier Science Ltd., Great Britain.

Chen, et al.: Sympathetic nerve sprouting, electrical remodeling and the mechanisms of sudden cardiac death. *Cardiovasc Res* 2001;50:409-416.

Cheng, et al.: Upregulation of functional beta(3)-adrenergic receptor in the failing canine myocardium. *Circ Res* 2001;89:599-606.

Chou, et al.: Effects of procainamide on electrical activity in the thoracic veins and the atria in canine model of sustained atrial fibrillation. *Am J Physiol* 2004;286:H1936-H1945.

Chou, et al.: Marshall bundle and the valve of Vieussens. *J Cardiovasc Electrophysiol* 2003;14:1254.

Chudin et al., "Intracellular $Ca^{2+}$ Dynamics and the Stability of Ventricular Tachycardia," *Biophysical Journal*, Dec. 1999, pp. 2930-2941, vol. 77, Biophysical Society.

Creamer et al., "Acute and Chronic Effects of Sotalol and Propranolol on Ventricular Repolarization Using Constant-Rate Pacing," *Am. J. Cardiol.*, May 1, 1986, pp. 1092-1096, vol. 57.

Dae et al., "Heterogeneous Sympathetic Innervation in German Shepherd Dogs With Inherited Ventricular Arrhythmia and Sudden Cardiac Death," *Circulation*, Aug. 19, 1997, pp. 1337-1342, vol. 96, No. 4, American Heart Association, USA.

Dae, et at.: Scintigraphic assessment of MIBG uptake in globally denervated human and canine hearts—implications for clinical studies. *J Nucl Med* 1992;33:1444-1450.

Davey P: QT interval and mortality from coronary artery disease. *Prog Cardiovasc Dis* 2000;42:359-384.

Dincer et al., "The Effect of Diabetes on Expression of $β_1$-, $β_2$-, and $β_3$-Adrenoreceptors in Rat Hearts," *Diabetes*, Feb. 2001, pp. 455-461, vol. 50.

Donckier et al., "Cardiovascular effects of beta 3-adrenoceptor stimulation in perinephritic hypertension," *European Journal of Clinical Investigation*, 2001, pp. 681-689, vol. 31, Blackwell *Science* Ltd.

Doshi, et at: Initial experience with an active-fixation defibrillation electrode and the presence of nonphysiological sensing. *PACE* 2001;24:1713-20.

Duff et al., "Electrophysiologic Actions of High Plasma Concentrations of Propranolol in Human Subjects," *Journal of the American College of Cardiology*, Dec. 1983, pp. 1134-1140, vol. 2, No. 6, American College of Cardiology, Elsevier Biomedical, USA.

Eckardt et al., "Arrhythmias in Heart Failure: Current Concepts of Mechanisms and Therapy," *Journal of Cardiovascular Electrophysiology*, Jan. 2000, pp. 106-117, vol. 11, No. 1, Futura Publishing Company Inc., Armonk, NY, USA.

Edvardsson et al., "Effects of acute and chronic beta-receptor blockade on ventricular repolarisation in man," *British Heart Journal*, Jun. 1981, pp. 628-636, vol. 45, No. 6, British Medical Association, UK.

Eldar, et al.: Significance of paroxysmal atrial fibrillation complicating acute myocardial infarction in the thrombolytic era. SPRINT and Thrombolytic Survey Groups. *Circulation* 1998;97:965-970.

Farrukh et al., "Up-Regulation of $Beta_2$-Adrenergic Receptors in Previously Transplanted, Denervated Nonfailing Human Hearts," *Journal of the American College of Cardiology*, Dec. 1993, pp. 1902-1908, vol. 22, No. 7, Elsevier, USA.

Fozzard, "Afterdepolarizations and triggered activity," *Supplement to Basic Research in Cardiology*, 1992, pp. 105-113, vol. 87, Suppl. 2, Steinkopff Verlag Darmstadt Springer-Verlag, New York, NY, USA.

Franklin et al., "Control of Neuronal Size Homeostasis by Trophic Factor-mediated Coupling of Protein Degradation to Protein Synthesis," *The Journal of Cell Biology*, Sep. 7, 1998, pp. 1313-1324, vol. 142, No. 5, The Rockefeller University Press, USA.

Freemantle et al., "β Blockade after myocardial infarction: systematic review and meta regression analysis," *BMJ*, Jun. 26, 1999, pp. 1730-1737, vol. 318, UK.

Fu SY, Gordon T: The cellular and molecular basis of peripheral nerve regeneration. *Mol.Neurobiol.* 1997;14:67-116.

Gang, et al.: Short coupled premature ventricular contraction initiating ventricular fibrillation in a patient with Brugada syndrome. *J Cardiovasc Electrophysiol* 2004;15:837.

Garfinkel, et al.: Preventing ventricular fibrillation by flattening cardiac restitution. *Proc Natl Acad Sci U S A* 2000;97:6061-66.

Gauthier et al., "Interspecies Differences in the Cardiac Negative Inotropic Effects of $β_3$-Adrenoceptor Agonists," *The Journal of Pharmacology and Experimental Therapeutics*, 1999, pp. 687-693, vol. 290, The American Society for Pharmacology and Experimental Therapeutics, USA.

Gauthier et al.: Beta3-adrenoceptors in the cardiovascular system. *Trends Pharmacol Sci.* 2000;21:426-431.

Gauthier et al. : The negative inotropic effect of beta3-adrenoceptor stimulation is mediated by activation of a nitric oxide synthase pathway in human ventricle. *Supplement to Circulation, Abstracts from the 70th Scientific Sessions*, Nov. 9-12, 1997, p. 283, vol. 96, No. 8, American Heart Association, USA.

Gauthier, et al.: Functional β3-adrenoceptor in the human heart. *J Clin Invest* 1996;98:556-562.

Giacobino JP: Beta 3-adrenoceptor: an update. *Eur J Endocrinol* 1995;132:377-85.

Ginty DD, Segal RA: Retrograde neurotrophin signaling: Trk-ing along the axon. *Curr.Opin.Neurobiol.* 2002;12:268-274.

Goldberg, et al.: Impact of atrial fibrillation on the in-hospital and long-term survival of patients with acute myocardial infarction: A community-wide perspective. *Am Heart J* 1990;119:996-1001.

Gottlieb et al., "Effect of Beta-Blockade on Mortality Among High-Risk and Low-Risk Patients After Myocardial Infarction," *The New England Journal of Medicine*, Aug. 20, 1998, pp. 489-497, vol. 339, No. 8, Massachusetts Medical Society, Boston, MA, USA.

Guth L: Regeneration in the mammalian peripheral nervous system. *Physiol Rev* 1956;36:441-478.

Hamabe, et al.: Correlation between anatomy and electrical activation in canine pulmonary veins. *Circulation* 2003;107:1550-1555.

Hamzei, et al.: The role of approximate entropy in predicting ventricular defibrillation threshold. *J Cardiovasc Pharmacol Ther* 2002;7:45-52.

Harding et al., "Lack of evidence for β3-adrenoceptor modulation of contractile function in human ventricular myocytes," *Supplement to Circulation, Abstracts from the 70th Scientific Sessions*, Nov. 9-12, 1997, p. 284, vol. 96, No. 8, American Heart Association, USA.

Hartikainen, et al.: Sympathetic reinnervation after acute myocardial infarction. *Am J Cardiol* 1996;77:5-9.

Hassankhani, et al: Overexpression of NGF within the heart of transgenic mice causes hyperinnervation, cardiac enlargement, and hyperplasia of ectopic cells. *Dev Biol* 1995;169:309-321.

Hayashi H, et al.: Effects of cytochalasin D on electrical restitution and the dynamics of ventricular fibrillation in isolated rabbit heart. *J Cardiovasc Electrophysiol* 2003;14:1077-1084.

Hayashi, et al.: Aging-related increase to inducible atrial fibrillation in the Rat Model. *J Cardiovasc Electrophysiol* 2002;13:801-808.

Heath et al., "Overexpression of nerve growth factor in the heart alters ion channel activity and β-adrenergic signalling in an adult transgenic mouse," *Journal of Physiology*, 1998, pp. 779-791, vol. 512.3.

Heid et al., "Genome Methods: Real Time Quantitative PCR," *Genome Research*, 1996, pp. 986-994, vol. 6, Cold Spring Harbor Laboratory Press.

Hjalmarson, "Effects of Beta Blockade on Sudden Cardiac Death During Acute Myocardial Infarction and the Postinfarction Period," *The American Journal of Cardiology*, Nov. 13, 1997, pp. 35J-39J, vol. 80(9B), Excerpta Medica, Inc., USA.

Hom et al., "$β_3$-Adrenoceptor Agonist-Induced Increases in Lipolysis, Metabolic Rate, Facial Flushing, and Reflex Tachycardia in Anesthetized Rhesus Monkeys," *The Journal of Pharmacology and Experimental Therapeutics*, 2001, pp. 299-307, vol. 297, American Society for Pharmacology and Experimental Therapeutics.

Hume, et al.: Chloride conductance pathways in heart. *Am J Physiol* 1991;261:C399-C412.

Hwang, et al.: Radiofrequency ablation of accessory pathways guided by the location of the ligament of Marshall. *J Cardiovasc Electrophysiol* 2003;14:616-620.

Hwang, et al.: Vein of Marshall cannulation for the analysis of electrical activity in patients with focal atrial fibrillation. *Circulation* 2000;101:1503-1505.

Ieda, et al.: Endothelin-1 regulates cardiac sympathetic innervation in the rodent heart by controlling nerve growth factor expression. *J.Clin.Invest* 2004;113:876-884.

Ihl-Vahl et al., "Differential Regulation of mRNA Specific for $β_1$- and $β_2$-adrenergic Receptors in Human Failing Hearts. Evaluation of the Absolute Cardiac mRNA Levels by Two Independent Methods," *J. Mol. Cell. Cardiol.*, 1996, pp. 1-9, vol. 28, Academic Press Limited.

Ihl-Vahl et al., "Regulation of β-Adrenergic Receptors in Acute Myocardial Ischemia: Subtype-selective increase of mRNA Specific for $β_1$-Adrenergic Receptors," *J. Mol. Cell. Cardiol.*, 1995, pp. 437-452, vol. 27, Academic Press Limited.

Janse, et al: Effects of unilateral stellate ganglion stimulation and ablation on electrophysiologic changes induced by acute myocardial ischemia in dogs. *Circulation* 1985;72:585-595.

Jardine, et al.: A neural mechanism for sudden death after myocardial infarction. *Clin.Auton.Res.* 2003;13:339-341.

Josephson, et al.: The beta subunit increases Ca2+ currents and gating charge movements of human cardiac L-type Ca2+ channels. *Biophys J* 1996;70:1285-1293.

Kadish, et a.: Paradoxical effects of exercise on the QT interval in patients with polymorphic ventricular tachycardia receiving type Ia antiarrhythmic agents. *Circulation* 1990;81:14-19.

Kaplan DR,: Neurotrophin signal transduction in the nervous system. *Curr Opin Neurobiol* 2000;10:381-391.

Kathofer, et al.: Functional coupling of human beta 3-adrenoreceptors to the KvLQT1/MinK potassium channel. *J Biol Chem* 2000;275:26743-26747.

Kaumann et al., "Modulation of human cardiac function through 4 β-adrenoceptor populations," *Naunyn-Schmiedeberg's Arch Pharmacol.*, Jan. 22, 1997, pp. 667-681, 355, Springer-Verlag.

Kawashima et al., "Contrasting Effects of Dopamine and Dobutamine on Myocardial Release of Norepinephrine during Acute Myocardial Infarction," *Japanese Heart Journal*, Nov. 1985, pp. 975-984, vol. 26, No. 6, Japanese Heart Journal Association, Tokyo, Japan.

Kaye, et al.: Reduced myocardial nerve growth factor expression in human and experimental heart failure. *Circ Res* 2000;86:E80-E84.

Kihara et al., "Intracellular Calcium and Ventricular Fibrillation," *Circulation Research*, May 1991, pp. 1378-1389, vol. 68, No. 5, American Heart Association, USA.

Kim, et al.: Sympathetic nerve sprouting after orthotopic heart transplantation. *J Heart Lung Transplantation* 2004;23:1349-1358.

Kim, et al.: The Ligament of Marshall: A structural analysis in human hearts with implications for atrial arrhythmias. *J Am Coll Cardiol.* 2000;36:1324-7.

Kirkness et al., "The Dog Genome: Survey Sequencing and Comparative Analysis," *Science*, Sep. 26, 2003, pp. 1898-1903, vol. 301.

Kitamura et al., "The Negative Inotropic Effect of $β_3$-Adrenoceptor Stimulation in the Beating Guinea Pig Heart," *Journal of Cardiovascular Pharmacology*, May 2000, pp. 786-790, vol. 35, Lippincott Williams & Wilkins, Inc., Philadelphia, PA, USA.

Kleiger, et al.: Decreased heart rate variability and its association with increased mortality after acute myocardial infarction. *Am J Cardiol* 1987;59:256-262.

Kohout et al., "Augmentation of Cardiac Contractility Mediated by the Human $β_3$-Adrenergic Receptor Overexpressed in the Hearts of Transgenic Mice," *Circulation*, Nov. 13, 2001, pp. 2485-2491, vol. 104, The American Heart Association, USA.

Kong JR, et al.: Circadian variation in human ventricular refractoriness. *Circulation* 1995;92:1507-1516.

Korsching S: The neurotrophic factor concept: a reexamination. *J.Neurosci.* 1993;13:2739-2748.

Korsching, et al.: Nerve growth factor in sympathetic ganglia and corresponding target organs of the rat: correlation with density of sympathetic innervation. *Proc Natl Acad Sci* 1983;80:3513-3516.

Korsching, et al: Developmental changes of nerve growth factor levels in sympathetic ganglia and their target organs. *Dev Biol* 1988;126:40-46.

Kotzbauer, et al.: Postnatal development of survival responsiveness in rat sympathetic neurons to leukemia inhibitory factor and ciliary neurotrophic factor. *Neuron* 1994;12:763-773.

La Rovere, et al.: Baroreflex sensitivity and heart rate variability in the identification of patients at risk for life-threatening arrhythmias : implications for clinical trials. *Circulation* 2001;103:2072-2077.

Lai, et al.: Co-localization of tenascin and sympathetic nerves in a canine model of nerve sprouting and sudden cardiac death. *J Cardiovasc Electrophysiol* 2000; 11:1345-51.

Lampert, et al.: Circadian variation of sustained ventricular tachycardia in patients with coronary artery disease and implantable cardioverter-defibrillators. *Circulation* 1994;90:241-247.

Lavian, et al: In vivo extracellular recording of sympathetic ganglion activity in a chronic animal model. *Clin.Auton.Res.* 2003; 13 Suppl 1:183-188.

Leblais et al., "$\beta_3$-Adrenoceptor Control the Cystic Fibrosis Transmembrane Conductance Regulator through a cAMP/Protein Kinase A-independent Pathway," *The Journal of Biological Chemistry,* Mar. 5, 1999, pp. 6107-6113, vol. 274, No. 10, The American Society for Biochemistry and Molecular Biology, Inc., USA.

Lee, et al.: Effects of diacetyl monoxime and cytochalasin D on ventricular fibrillation in swine right ventricles. *Am J Physiol* 2001;280:H2689-96.

Lee, et al.: Patterns of wave break during ventricular fibrillation in isolated swine right ventricle. *Am J Physiol* 2001;281:H253-265.

Levi-Montalcini R: Growth control of nerve cells by a protein factor and its antiserum. *Science* 1964;143:105-110.

Li W, et al.: Infarction alters both the distribution and noradrenergic properties of cardiac sympathetic neurons. *Am.J Physiol Heart Circ. Physiol* 2004;286:H2229-36.

Liggett SB et al.: Structural basis for receptor subtype-specific regulation revealed by a chimeric beta 3/beta 2-adrenergic receptor. *Proc Natl Acad Sci USA.* 1993;90:3665-3669.

Lin, et al.: Slowing of intestinal transit by fat or peptide YY depends on a beta-adrenergic pathway. *Am J Physiol* 2003;285(6):GI310-6.

Lindholm, et al.: Interleukin-1 regulates synthesis of nerve growth factor in non-neuronal cells of rat sciatic nerve. *Nature* 1987;330:658-659.

Liu, et al.: Coexistence of two types of ventricular fibrillation during acute regional ischemia in rabbit ventricle. *J Cardiovasc Electrophysiol* 2004;15:1433-1440.

Liu, et al.: Spatiotemporal correlation between phase singularities and wavebreaks during ventricular fibrillation. *J Cardiovasc Electrophysiol* 2003; 14:1103-1109.

Liu, et al.: Sympathetic nerve sprouting, electrical remodeling and increased vulnerability to ventricular fibrillation in hypercholesterolemic rabbits. *Circ Res* 2003;92: 1145-1152.

Lowell et al, "The Potential Significance of $\beta_3$ Adrenergic Receptors," *The Journal of Clinical Investigation,* Mar. 1995, p. 923, vol. 95, No. 3, American Society for Clinical Investigation, Inc., The Rockefeller University Press, USA.

Lucchesi, et al.: Pharmacological modification of arrhythmias after experimentally induced acute myocardial infarction. Drugs acting on the nervous system. *Circulation* 1975;52:III241-III247.

Maisel, et al.: Externalization of beta-adrenergic receptors promoted by myocardial ischemia. *Science* 1985;230:183-186.

Malik, et al.: Depressed heart rate variability identifies postinfarction patients who might benefit from prophylactic treatment with amiodarone: a substudy of EMIAT (The European Myocardial Infarct Amiodarone Trial). *J Am Coll Cardiol* 2000;35:1263-1275.

Malkin, et al.: The effect of inducing ventricular fibrilation with 50-hz pacing versus T wave simulation on the ability to defibrillate. *PACE,* 21:1093-1097 (May 1998).

Mallavarapu, et al.: Circadian variation of ventricular arrhythmia recurrences after cardioverter-defibrillator implantation in patients with healed myocardial infarcts. *Am J Cardiol* 1995;75:1140-1144.

Malpas SC: The rhythmicity of sympathetic nerve activity. *Prog. Neurobiol.* 1998;56:65-96.

Marks, "Cardiac Intracellular Calcium Release Channels: Role in Heart Failure," *Circulation Research,* 2000, pp. 8-11, vol. 87, American Heart Association, USA.

Marron et al., "Distribution, Morphology, and Neurochemistry of Endocardial and Epicardial Nerve Terminal Arborizations in the Human Heart," Oct. 15, 1995, pp. 2343-2351, vol. 92, No. 8, American Heart Association, USA.

Menasche, et al.: Autologous skeletal myoblast transplantation for severe postinfarction left ventricular dysfunction. *J Am Coll Cardiol* 2003;41:1078-1083.

Merillat et al., "Role of Calcium and the Calcium Channel in the Initiation and Maintenance of Ventricular Fibrillation," *Circulation Research,* Nov. 1990, pp. 1115-1123, vol. 67, No. 5, American Heart Association, USA.

MERIT-HF Study Group, "Effect of metoprolol CR/XL in chronic heart failure: Metoprolol CR/XL Randomised Intervention Trial in Congestive Heart Failure (MERIT-HF)," *The Lancet,* Jun. 12, 1999, pp. 2001-2007, vol. 353, UK.

Middlekauff, et al.: Morning sympathetic nerve activity is not increased in humans: Implications for mechanisms underlying the circadian pattern of cardiac risk. *Circulation* 1995;91:2549-2555.

Miknyoczki et al., "The Neurotrophin-Trk Receptor Axes Are Critical for the Growth and Progression of Human Prostatic Carcinoma and Pancreatic Ductal Adenocarcinoma Xenografts in Nude Mice," *Clinical Cancer Research,* Jun. 2002, pp. 1924-1931, vol. 8.

Minardo, et al.: Scintigraphic and electrophysiological evidence of canine myocardial sympathetic denervation and reinnervation produced by myocardial infarction or phenol application. *Circulation* 1988;78:1008-1019.

Miyauchi, et al.: Altered atrial electrical restitution and heterogeneous sympathetic hyperinnervation in hearts with chronic left ventricular myocardial infarction: implications to atrial fibrillation. *Circulation* 2003;108:360-366.

Mohell et al.: The β-adrenergic radioligand [3H]CGP-12177, generally classified as an antagonist, is a thermogenic agonist in brown adipose tissue. Biochem. J.(1989), 261:401-5.

Moïse et al., "An Animal Model of Spontaneous Arrhythmic Death," *Journal of Cardiovascular Electrophysiology,* Jan. 1997, pp. 98-103, vol. 8.

Moniotte et al., "Upregulation of $\beta_3$-Adrenoceptors and Altered Contractile Response to Inotropic Amines in Human Failing Myocardium," *Circulation,* 2001, pp. 1649-1655, vol. 103, American Heart Association, USA.

Mukherjee, et al.: Beta adrenergic and muscarinic cholinergic receptors in canine myocardium. Effects of ischemia. *J.Clin.Invest* 1979;64:1423-1428.

Mukherjee, et al.: Relationship between beta-adrenergic receptor numbers and physiological responses during experimental canine myocardial ischemia. *Circ.Res.* 1982;50:735-741.

Muller, et al.: Circadian variation in the frequency of sudden cardiac death. *Circulation* 1987;75:131-138.

Myerburg et al., "Frequency of Sudden Cardiac Death and Profiles of Risk," *The American Journal of Cardiology,* Sep. 11, 1997, pp. 10F-19F, vol. 80 (5B), Excerpta Medica, Inc., USA.

Nademanee, et al: Treating electrical storm: sympathetic blockade versus advanced cardiac life support-guided therapy. *Circulation* 2000;102:742-747.

Nitta, et al.: Propentofylline prevents neuronal dysfunction induced by infusion of anti-nerve growth factor antibody into the rat septum. *Eur.J Pharmacol.* 1996;307:1-6.

Nori, et al.: Immunohistochemical evidence for sympathetic denervation and reinnervation after necrotic injury in rat myocardium. *Cell Mol Biol* 1995;41:799-807.

Oh et al., "Relationship between nerve sprouting and neurotrophic gene expression in a mouse model of myocardial infarction," *Heart Rhythm,* May Supp. 2004, p. S191, Abstract No. 608, vol. 1, No. I.

Oh, et al.: Scar formation after ischemic myocardial injury in MRL mice. *Cardiovasc Pathol* 2004;13:203-6.

Ohara, et al.: Downregulation of Immunodetectable Atrial Connexin40 in a Canine Model of Chronic Left Ventricular Myocardial Infarction: Implications to Atrial Fibrillation. *J Cardiovasc Pharmacol Ther* 2002;7:89-94.

Ohara, et al.: Increased vulnerability to inducible atrial fibrillation caused by partial cellular uncoupling with heptanol. *Am J Physiol* 2002;283:H1116-1122.

Ohara, et al.: Increased wave break during ventricular fibrillation in the epicardial border zone of hearts with healed myocardial infarction. *Circulation* 2001;103 1465-1472.

Ohyanagi, et al: Beta-adrenergic receptors in ischemic and nonischemic canine myocardium: relation to ventricular fibrillation and effects of pretreatment with propranolol and hexamethonium. *J.Cardiovasc.Pharmacol.* 1988;11:107-114.

Okin, et al: Assessment of QT Interval and QT Dispersion for Prediction of All-Cause and Cardiovascular Mortality in American Indians: The Strong Heart Study. *Circulation* 2000;101:61-66.

Okuyama, et al.: High resolution mapping of the pulmonary vein and the vein of marshall during induced atrial fibrillation and atrial tachycardia in a canine model of pacing-induced congestive heart failure. *J Am Coll Cardiol* 2003;42:348-60.

Okuyama, et al.: Nerve sprouting induced by radiofrequency catheter ablation in dogs. *Heart Rhythm* 2004; 1:712-7.

Oliver, Michael, "Metabolic Causes and Prevention of Ventricular Fibrillation During Acute Coronary Syndromes" (*The American Journal of Medicine*, 112 (4) Mar. 2002: pp. 305-311).

Omichi et al., "Transmembrane $Ca^{2+}$ Transients and Action Potential Duration Restitution are Two Independent but Coupled Phenomena in Ventricular Fibrillation," Supplement to *Circulation*, Abstracts from Scientific Sessions 2000, Oct. 31, 2000, p. 1672, vol. 102, No. 18, American Heart Association, USA.

Omichi, et al.: Comparing cardiac action potentials recorded with metal and glass microelectrodes. *Am J Physiol* 2000 279;H3113-3117.

Omichi, et al.: Demonstration of electrical and anatomical connections between Marshall bundles and left atrium in dogs: implications on the generation of P waves on surface electrocardiogram. *J Cardiovasc Electrophysiol* 2002;13:1283-1291.

Omichi, et al.: Effects of amiodarone on wave front dynamics during ventricular fibrillation in isolated swine right ventricle. *Am J Physiol* 2002;282:H 1063-1070.

Omichi, et al.: Intracellular Ca dynamics in ventricular fibrillation. *Am J Physiol* 2004;286:H1836-H1844.

Packer et al., "The Effect of Carvedilol on Morbidity and Mortality in Patients with Chronic Heart Failure," *The New England Journal of Medicine*, May 23, 1996, pp. 1349-1355, vol. 334, No. 21, Massachusetts Medical Society, Boston, MA, USA.

Pak, et al.: Catheter ablation of ventricular fibrillation in rabbit ventricles treated with beta-blockers. *Circulation* 2003;108:3149-56.

Pak, et al.: Improvement of defibrillation efficacy with pre-shock synchronized pacing. *J Cardiovasc Electrophysiol* 2004; 2004;15:581-587.

Pak, et al.: Mesenchymal stem cell injection induces cardiac nerve sprouting and increased tenascin expression in a swine model of myocardial infarction. *J Cardiovasc Electrophysiol.* 2003;14:841-48.

Pak, et al.: Synchronization of ventricular fibrillation with real-time feedback pacing: Implication to low-energy defibrillation. *Am J Physiol* 2003;285:H2704-2711.

Park, et al.: Distribution of cardiac nerves in patients with diabetes mellitus: an immunohistochemical postmortem study of human hearts. *Cardiovasc Path* 2002;11:326-331.

Park, et al.: Thoracic vein ablation terminates chronic atrial fibrillation in dogs. *Am J Physiol Heart Circ Physiol.* 2004;286(6):H2072-7.

Parry, et al.: Incidence and functional significance of sympathetic reinnervation after cardiac transplantation. *Transplant Proc* 1997;29:569-570.

Peckova, et al.: Weekly and seasonal variation in the incidence of cardiac arrests. *Am.Heart J.* 1999;137:512-515.

Pedersen, et al.: The occurrence and prognostic significance of atrial fibrillation/-flutter following acute myocardial infarction. TRACE Study group. TRAndolapril Cardiac Evaluation. *Eur Heart J* 1999;20:748-754.

Perry, et al.: Late ventricular arrhythmia and sudden death following direct-current catheter ablation of the atrioventricular junction. *Am.J. Cardiol.* 1992;70:765-768.

Peters RW: Propranolol and the morning increase in sudden cardiac death: (the beta-blocker heart attack trial experience). *Am.J.Cardiol.* 1990;66:57G-59G.

Podio et al.: Regional sympathetic denervation after myocardial infarction: a follow-up study using [123]MIBG. *Q J Nucl Med* 1995;39:40-43.

Postma et al., "Absence of Calsequestrin 2 Causes Severe Forms of Catecholaminergic Polymorphic Ventricular Tachycardia," *Circulation Research*, 2002, pp. e21-e26, vol. 91, American Heart Association, USA.

Priori et al., "Clinical and Molecular Characterization of Patients with Catecholaminergic Polymorphic Ventricular Tachycardia," *Circulation*, Jul. 2, 2002, pp. 69-74, vol. 106, American Heart Association, USA.

Qin, et al.: Loss of cardiac sympathetic neurotransmitters in heart failure and NE infusion is associated with reduced NGF. *Am J Physiol Heart Circ Physiol* 2002:282:H363-H371.

Qu, et al.: Mechanisms of discordant alternans and induction of reentry in a simulated cardiac tissue. *Circulation* 2000; 102:1664-70.

Rathore, et al.: Acute myocardial infarction complicated by atrial fibrillation in the elderly: prevalence and outcomes. *Circulation* 2000;101:969-974.

Reiken et al., "β-Blockers Restore Calcium Release Channel Function and Improve Cardiac Muscle Performance in Human Heart Failure," *Circulation*, 2003, pp. 2459-2466, vol. 107, American Heart Association, Inc., USA.

Reiter, "β-Adrenergic Blocking Drugs as Antifibrillatory Agents," *Current Cardiology Reports*, 2002, pp. 426-433, vol. 4, Current *Science*, Inc.

Robinson, et al.: "Immunocytochemistry," *Theory and Practice of Histological Techniques*. Third Edition. Churchill Livingstone, Edinburgh London, Melbourne and New York, 1990, pp. 413-436.

Rodenbaugh et at, "Increased Susceptibility to Ventricular Arrhythmias in Hypertensive Paraplegic Rats," *Clinical and Experimental Hypertension*, 2003, pp. 349-358, vol. 25, Marcel Dekker, Inc., New York, NY, USA.

Rosenbaum, et al.: Predicting sudden cardiac death from T wave alternans of the surface electrocardiogram: promise and pitfalls. *J.Cardiovasc.Electrophysiol.* 1996;7:1095-1111.

Rush RA: Immunohistochemical localization of endogenous nerve growth factor. *Natul8re* 1984;312:364-367.

Sanguinetti, et al.: Coassembly of KvLQTI and minK (IsK) proteins to form cardiac I(Ks) potassium channel. *Nature* 1996;384:80-83.

Schwartz PJ: QT prolongation, sudden death, and sympathetic imbalance: the pendulum swings. *J Cardiovasc Electrophysiol* 2001;12:1074-1077.

Schwartz, et al.: Autonomic mechanisms in ventricular fibrillation induced by myocardial ischemia during exercise in dogs with healed myocardial infarction. An experimental preparation for sudden cardiac death. *PubMed Abstract of Circulation* Apr;69(4):790-800(1984).

Schwartz, et al.: Autonomic mechanisms and sudden death. New insights from analysis of baroreceptor reflexes in conscious dogs with and without a myocardial infarction. *Circulation* 1988;78:969-979.

Schwartz, et al.: Autonomic nervous system and sudden cardiac death: Experimental basis and clinical observations for post-myocardial infarction risk stratification. *Circulation* 1992;85[Suppl. I]: I-77-I-91.

Schwartz, et al.: Effects of unilateral stellate ganglion blockade on the arrhythmias associated with coronary occlusion. *Am Heart J* 1976;92:589-599.

Schwartz, et al.: Left cardiac sympathetic denervation in the management of high-risk patients affected by the long-QT syndrome. *Circulation* 2004; 109:1826-1833.

Schwartz, et al.: Left cardiac sympathetic denervation in the therapy of congenital long QT syndrome. A worldwide report. *Circulation* 1991;84:503-511.

Schwartz, et al.: Prevention of sudden cardiac death after a first myocardial infarction by pharmacologic or surgical antiadrenergic interventions. *J Cardiovasc Electrophysiol* 1992;3:2-16.

Schwartz, et al.: Sympathetic nervous system and cardiac arrhythmias, in Zipes DP, Jalife J (eds): *Cardiac Electrophysiology: From Cell to Bedside.* Philadelphia, PA, W. B. Saunders Company, 1990, pp. 330-343.

Schwartz, et al.: The long QT syndrome, in Zipes DP, Jalife J (eds): *Cardiac Electrophysiology: From Cell to Bedside.* Philadelphia, W. B. Saunders Company, 1994, pp. 788-811.

Scoote et al., "The cardiac ryanodine receptor (calcium release channel): Emerging role in heart failure and arrhythmia pathogenesis," *Cardiovascular Research,* 2002, pp. 359-372, vol. 56, Elsevier *Science B.V.*

Shen et al., "Differences in $\beta_3$-Adrenergic Receptor Cardiovascular Regulation in Conscious Primates, Rats and Dogs," *The Journal of Pharmacology and Experimental Therapeutics,* 1996, pp. 1435-1443, vol. 278, No. 3, The American Society for Pharmacology and Experimental Therapeutics, USA.

Shimizu, et al.: Cellular basis for the ECG features of the LQT1 form of the long-QT syndrome: effects of beta-adrenergic agonists and antagonists and sodium channel blockers on transmural dispersion of repolarization and torsade de pointes. *Circulation* 1998;98:2314-2322.

Shimizu, et al.: Differential effects of beta-adrenergic agonists and antagonists in LQT1, LQT2 and LQT3 models of the long QT syndrome. *J Am Coll Cardiol* 2000;35:778-786.

Shimizu, et al.: Sympathetic modulation of the long QT syndrome. *Eur.Heart J.* 2002;23:1246-1252.

Shivkumar, et al.: Sudden death after heart transplantation: the major mode of death. *J Heart Lung Transplant* 2001;20:180(abstract).

Sjoberg, et al.: The initial period of peripheral nerve regeneration and the importance of the local environment for the conditioning lesion effect. *Brain Res* 1990;529:79-84.

Sosunov et al., "Abnormal cardiac repolarization and impulse initiation in German shepherd dogs with inherited ventricular arrhythmias and sudden death," *Cardiovascular Research,* 1999, pp. 65-79, vol. 42, Elsevier *Science B.V.*

Stanton, et al.: Regional sympathetic denervation after myocardial infarction in humans detected noninvasively using 1-123-metaiodobenzylguanidine. *J Am Coll Cardiol* 1989;14:1519-1526.

Strasser, et al.: Sensitization of the beta-adrenergic system in acute myocardial ischaemia by a protein kinase C-dependent mechanism. *Eur.Heart J.* 1991; 12 Suppl F:48-53.

Strohmer, et al.: Radiofrequency ablation of focal atrial tachycardia and atrioatrial conduction from recipient to donor after orthotopic heart transplantation. *J Cardiovasc Electrophysiol* 2000;11:1165-9.

Strohmer, et al.: Selective atrionodal input ablation for induction of proximal complete heart block with stable junctional escape rhythm in patients with uncontrolled atrial fibrillation. *J Interv Card Electrophysiol* 2003;8:49-57.

Sutula, et al.: Mossy fiber synaptic reorganization in the epileptic human temporal lobe. *Ann Neurol* 1989;26:321-330.

Sutula, et al.: Synaptic reorganization in the hippocampus induced by abnormal functional activity. *Science* 1988;239:1147-1150.

Sutherland et. al: Acid-sensing ion channel 3 matches the acid-gated current in cardiac ischemia-sensing neurons. The Volume Institute, Oregon Health Sciences University, Portland, OR 97201-3098, pp. 1-10.

Swan, et al.: Sinus node function and ventricular repolarization during exercise stress test in long QT syndrome patients with KvLQT1 and HERG potassium channel defects. *J Am Coll Cardiol* 1999;34:823-829.

Swissa et al., "Long-Term Subthreshold Electrical Stimulation of the Left Stellate Ganglion and a Canine Model of Sudden Cardiac Death," *Journal of the American College of Cardiology,* Mar. 3, 2004, pp. 858-864, vol. 43, No. 5, Elsevier Inc., USA.

Swissa, et al.: Sildenafil-nitric oxide donor combination promotes ventricular tachyarrhythmias in the swine right ventricle. *Am J Physiol* 2002;282:H1787-1792.

Swissa. et al.: Action potential duration restitution and ventricular fibrillation due to rapid focal excitation. *Am J Physiol* 2002;282:H1915-1923.

Takei, et al.: The autonomic control of the transmural dispersion of ventricular repolarization in anesthetized dogs. *J Cardiovasc Electrophysiol* 1999;10:981-989.

Task Force, et al.: Heart rate variability—standards of measurement, physiological interpretation, and clinical use. *Circulation* 1996;93:1043-1065.

Tato, et al.: Effects of right stellate ganglion stimulation on regional myocardial blood flow and ischemic injury in dogs. *Eur.J Pharmacol.* 1981;71:223-232.

Tavernier et al., "The Positive Chronotropic Effect Induced by BRL 37344 and CGP 12177, Two *Beta*-3 Adrenergic Agonists, Does Not Involve Cardiac *Beta* Adrenoceptors but Baroreflex Mechanisms," *The Journal of Pharmacology and Experimental Therapeutics,* Dec. 1992, pp. 1083-1090, vol. 263, No. 3, The American Society for Pharmacology and Experimental Therapeutics, Williams & Wilkins, USA.

Tavernier et al., "$\beta_3$-Adrenergic stimulation produces a decrease of cardiac contractility ex vivo in mice overexpressing the human $\beta_3$-adrenergic receptor," *Cardiovascular Research,* 2003, pp. 288-296, vol. 59, *European Society of Cardiology,* Elsevier B.V.

Thandroyen, et al.: Alterations in beta-adrenergic receptors, adenylate cyclase, and cyclic AMP concentrations during acute myocardial ischemia and reperfusion. *Circulation* 1990;82:II30-II37.

Tsai, et al.: T-wave alternans as a predictor of spontaneous ventricular tachycardia in a canine model of sudden cardiac death. *J Cardiovasc Electrophsiol* 2002;13:51-55.

Uchida, et al.: Sustained decrease in coronary blood flow and excitation of cardiac sensory fibers following sympathetic stimulation. *Jpn.Heart J* 1975;16:265-279.

Ure: Retrograde transport and steady-state distribution of 1251-nerve growth factor in rat sympathetic neurons in compartmented cultures. *J.Neurosci.* 1997;17:1282-1290.

Ursell et al., "Anatomic Distribution of Autonomic Neural Tissue in the Developing Dog Heart: I. Sympathetic Innervation," *The Anatomical Record,* Jan. 1990, pp. 71-80, vol. 226, No. 1, American Association of Anatomists, Wiley-Liss, USA.

Valderrábano et al., "Dynamics of Intramural and Transmural Reentry During Ventricular Fibrillation in Isolated Swine Ventricles," *Circulation Research,* Apr. 27, 2001, pp. 839-848, vol. 88, American Heart Association, Inc., USA.

Valderrábano, et al.: Obstacle-Induced transition from ventricular fibrillation to tachycardia in isolated swine right ventricles: Insights into the transition dynamics and implications for the critical mass. *J Am Coll Cardiol* 2000;36:2000-8.

Valderrábano, et al.: Spatial distribution of phase singularities in ventricular fibrillation. *Circulation* 2003;108:354-359.

Valderrábano, et al: Frequency analysis of ventricular fibrillation in swine ventricles. *Circ Res* 2002;90:213-222.

Varghese et al., "$\beta_3$-adrenoceptor deficiency blocks nitric oxide-dependent inhibition of myocardial contractility," *The Journal of Clinical Investigation,* Sep. 2000, pp. 697-703, vol. 106, No. 5, American Society for Clinical Investigation, USA.

Vassalle, et al.: The effect of adrenergic enhancement on overdrive excitation. *J.Electrocardiol.* 1976;9:335-343.

Verrier, et al.: Ventricular vulnerability during sympathetic stimulation: role of heart rate and blood pressure. *Cardiovasc Res* 1974;8:602-610.

Viskin, et al.: Circadian variation of symptomatic paroxysmal atrial fibrillation. Data from almost 10 000 episodes. *Eur Heart J* 1999;20:1429-1434.

Vleeming et al., "Density of β adrenoceptors in rat heart and lymphocytes 48 hours and 7 days after acute myocardial infarction," *Cardiovascular Research,* 1989, pp. 859-866, vol. 23.

Voroshilovsky, et al.: Mechanisms of ventricular fibrillation induction by 60 Hz alternating current in isolated swine right ventricle. *Circulation* 2000;102:1569-1574.

Vracko, et al.: Fate of nerve fibers in necrotic, healing, and healed rat myocardium. *Lab Invest* 1990;63:490-501.

Vracko, et al.: Nerve fibers in human myocardial scars. *Hum Pathol* 1991;22:138-146.

Wang, et al.: Optical mapping of ventricular defibrillation in isolated swine right ventricles: demonstration of a postshock isoelectric window after near-threshold defibrillation shocks. *Circulation* 2001; 104 227-233.

Willich, et al.: Circadian variation in the incidence of sudden cardiac death in the Framingham Heart Study population. *Am J Cardiol* 1987;60:801-806.

Wisser, et al.: Circadian changes of clinical chemical and endocrinological parameters. *J.Clin.Chem.Clin.Biochem.* 1981;19:323-337.

Wood, et al.: Circadian pattern of ventricular tachyarrhythmias in patients implantable cardioverter-defibrillators. *J Am Coll Cardiol* 1995;25:901-907.

Wu TJ, et al.: Mother rotors and the mechanisms of D600-induced type 2 ventricular fibrillation. *Circulation,* 2004;110:2110-2118.

Wu TJ, et al.: Progressive action potential duration shortening and the conversion from atrial flutter to atrial fibrillation in isolated canine right atrium. *J Am Coll Cardiol* 2001;38:1757-1765.

Wu TJ, et al.: Simultaneous biatrial computerized mapping during permanent atrial fibrillation in patients with organic heart diseases. *J Cardiovasc Electrophsiol* 2002; 13:571-577.

Wu, et al.: Pulmonary veins and ligament of Marshall as sources of rapid activations in a canine model of sustained atrial fibrillation. *Circulation* 2001; 103:1157-1163.

Wu, et al.: Two types of ventricular fibrillation in isolated rabbit hearts: importance of excitability and action potential duration restitution. *Circulation* 2002;106:1859-1866.

Yamashita, et al.: Circadian variation of cardiac K+ channel gene expression. *Circulation* 2003;107:1917-1922.

Yambe, et al.: Vagal nerve activity and the high frequency peak of the heart rate variability. *Int.J.Artif.Organs* 1999;22:324-328.

Yambe, et al.: Vagal nerve activity recording in the awake condition for the control of an artificial heart system. *Artif.Organs* 1999;23:529-531.

Yanowitz, et al.: Functional distribution of right and left stellate innervation to the ventricles. Production of neurogenic electrocardiographic changes by unilateral alteration of sympathetic tone. *Circ Res* 1966;18:416-428.

Yashima, et al.: Nicotine increases ventricular vulnerability to fibrillation in hearts with healed myocardial infarction. *Am J Physiol* (Heart and Circulatory Physiology) 2000; 278:H2124-33.

Yashima, et al.: On the Mechanism of the Probabilistic Nature of Ventricular Defibrillation Threshold. *Am J Physiol* 2003;284:H249-255.

Yip, et al.: Retrograde transport of nerve growth factor in lesioned goldfish retinal ganglion cells. *J Neurosci.* 1983;3:2172-2182.

Zhou, et al.: Low-affinity NGF receptor p75NTR immunoreactivity in the myocardium with sympathetic hyperinnervation. *J Cardiovasc Electrophysiol* 2004;15:430-7.

Zhou, et al.: Mechanisms of cardiac nerve sprouting after myocardial infarction in dogs. *Circ Res* 2004;95:76-83.

Zhou, et al.: Modulation of QT interval by cardiac sympathetic nerve sprouting and the mechanisms of ventricular arrhythmia in a canine model of sudden cardiac death. *J Cardiovasc Electrophsiol* 2001;12:1068-73.

Zhou, et al.: Nonreentrant focal activations in pulmonary veins in canine model of sustained atrial fibrillation. *Am J Physiol* 2002;283:H 1244-1252.

Zhou, et al.: Satellite-cell-derived nerve growth factor and neurotrophin-3 are involved in noradrenergic sprouting in the dorsal root ganglia following peripheral nerve injury in the rat. *Eur.J Neurosci.* 1999;11:1711-1722.

Zhou, et al.: Torsade de pointes and sudden death induced by thiopental and isoflurane anesthesia in dogs with cardiac electrical remodeling. *J Cardiovasc Pharmacol Ther* 2002;7:39-43.

Zipes et al., "Sudden Cardiac Death," *Circulation,* Nov. 24, 1998, pp. 2334-2351, vol. 98, No. 21, American Heart Association, USA.

\* cited by examiner

METHODS FOR THE PREDICTION OF ARRHYTHMIAS AND PREVENTION OF SUDDEN CARDIAC DEATH

RELATED APPLICATIONS

This application claims a priority to Provisional Application Ser. No. 60/741,172, filed on Nov. 30, 2005, which is incorporated herein by reference in its entirety.

GOVERNMENT INTEREST

This invention was made in part with government support under Grant R01 HL66389, awarded by the National Institutes of Health. The government may have certain rights to this invention.

FIELD OF THE INVENTION

The invention generally relates to medical diagnostic methods and kits for the prediction of cardiac arrhythmias and the prevention of sudden cardiac death.

BACKGROUND OF THE INVENTION

Sudden cardiac death (SCD) is a major public health problem that accounts for more than half of all cardiovascular deaths. SCD takes the lives of approximately 450,000 people in the United States each year, more than lung cancer, breast cancer, stroke, and AIDS combined. Most cases of SCD are due to ventricular arrhythmias and there is often an element of underlying ischemic heart disease. Ventricular tachycardia (VT) and ventricular fibrillation (VF) are different types of ventricular arrhythmias. VT is an abnormally fast ventricular heart rhythm which is, by itself, typically not fatal. VF is a chaotic ventricular heart rhythm which produces little or no net blood flow from the heart, such that there is little or not net blood flow to the brain and other organs. VF, if not terminated, results in death. Patient groups most at risk of ventricular arrhythmias leading to SCD include those with an acute or chronic myocardial infarction. Accordingly, deaths from SCD may be lowered by preventing the specific heart rhythm disturbances (ventricular arrhythmias) associated with it.

Different treatment options exist for SCD. The most common treatment includes implantable cardiac defibrillators (ICD) and drug therapy. Current ICD technology, however, only provides for the detection and recognition of an arrhythmia based on the sensed heart rate once it has already started. This leaves very little time to protect the individual from sudden cardiac death. Although there have been several attempts at developing new technology for predicting the onset of a cardiac arrhythmia, many of these methods and systems appear to rely primarily on events occurring within the heart, such as sensed heart rate and electrocardiography (ECG). For example, U.S. Pat. No. 6,308,094 discloses a method and device for predicting cardiac arrhythmias by gathering and processing electrocardiographic data, such as intervals between heart beats (RR-series) or other heart signals, to predict the occurrence of a cardiac arrhythmia. U.S. Pat. No. 6,516,219 discloses a method and apparatus for forecasting arrhythmia based on real-time intact intracardiac electrograms.

There currently exists no method of predicting cardiac arrhythmias well in advance of their occurrence that would allow for the institution of preventive and/or ameliorative therapy. A method and kit for predicting the occurrence of arrhythmias that allows preventive measures to prevent sudden cardiac death would thus represent a great advance in the art.

SUMMARY OF INVENTION

Methods and kits are provided for determining an increased likelihood of the occurrence of a cardiac arrhythmia, myocardial ischemia, and/or other diseased condition of the heart. The methods and kits disclosed herein generally comprise measuring the plasma and/or serum levels of nerve growth factor or NGF in a patient and detecting increases in plasma and/or serum level NGF as a predictor of cardiac arrhythmias. The methods of the present invention allow for the timely institution of preventive therapy for arrhythmia and/or SCD.

Any one or more pharmacologic agent(s) may be used in connection with the delivery of therapy. Such pharmacologic agents may include those which are effective in treating cardiac arrhythmias, myocardial ischemia, congestive heart failure, and any other diseased condition of the heart. Pharmacologic agents which may be used in connection with the delivery of anti-arrhythmic therapy may include, but are not limited to, those which are known to exert anti-arrhythmic effect, such as sodium channel blockers, $\beta$-blockers, potassium channel blockers, such as amiodarone and solatol, and calcium channel blockers, such as verapamil and diltiazem. Pharmacologic agents suitable for the treatment of myocardial ischemia may include, but are not limited to, statins, angiotensin-converting enzyme (ACE) inhibitors, aspirin, beta blockers, calcium channel blockers, and nitrates. Other suitable pharmacologic agents may include anti-convulsant agents, including but not limited to phenytoin, carbamazepine, valproate, and phenobarbitone, to name a few, which are believed to have anti-arrhythmic effect.

The methods and kits of the present invention permit the rapid, noninvasive detection and measurement of serum and/or plasma NGF for the prediction of an occurrence of arrhythmia and/or SCD requiring early therapeutic intervention. The above and other objects, features and advantages will become apparent to those skilled in the art from the following description of the preferred embodiments.

DESCRIPTION OF THE PREFERRED EMBODIMENTS

Methods and systems are disclosed for determining an increased likelihood of the occurrence of a cardiac arrhythmia and for the prevention of SCD. The methods and systems disclosed herein comprise measuring serum and/or plasma NGF levels of a patient and determining an increase in baseline serum and/or plasma NGF levels in the patient beyond normal values of about 10 ng/ml. In a preferred embodiment, the present invention provides a method for determining an increased likelihood of the occurrence of a cardiac arrhythmia comprising measuring serum and/or plasma NGF levels in a subject and detecting pan increase in said NGF levels. In another preferred embodiment of the present invention, a kit is provided for the rapid, non-invasive detection and measurement of serum and/or plasma NGF levels for the prediction of cardiac arrhythmias.

A significant advantage of the present invention is its speed and non-invasiveness. For example, patients' peripheral veins may be used to obtain small amounts of serum for detection and measurement of NGF levels. The present invention eliminates the need for invasive procedures and the test results can be almost instantly obtained.

The serum NGF levels of a patient may be monitored by assays well known in the art, such as, but not limited to, immunoassays, including enzyme-linked immunoassays (ELISA). Commercial kits are also available for measuring NGF levels. Commercially available NGF kits include the Promega NGF Emax® ImmunoAssay, for example, which provides optimized reagents and a protocol for the sensitive and specific detection of biologically active nerve growth factor. The assay uses horseradish peroxidase-conjugated secondary antibody and a single-component TMB substrate for the final chromogenic detection of bound NGF.

"NGF" or "nerve growth factor" described herein preferably refers to beta-NGF, and more preferably to the mature form of beta-NGF.

Antibodies useful in the immunoassay-based methods and kits of the present invention include polyclonal and monoclonal antibodies, chimeric, single chain, and humanized antibodies, as well as Fab fragments, including the products of a Fab or other immunoglobulin expression library. With respect to antibodies, the term, "immunologically specific" refers to antibodies that bind to one or more epitopes of NGF, but which do not substantially recognize and bind other molecules in a sample containing a mixed population of antigenic biological molecules.

Antibodies useful in the kits and methods of the present invention are those exhibiting specific binding affinity for NGF, i.e. the antibody binds to NGF with greater affinity than it binds to other compounds under specified conditions. Antibodies or antibody fragments having specific binding affinity to NGF may be used in kits and methods for detecting the presence and/or amount of NGF in a sample by contacting the sample with the antibody or antibody fragment under conditions such that an immunocomplex forms and detecting the presence and/or amount of the compound conjugated to the antibody or antibody fragment.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique that provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the target compound. The term "antibody fragment" also includes single charge antibodies.

The present invention provides antibodies capable of immunospecifically binding to NGF in order to measure plasma or serum NGF levels. Polyclonal or monoclonal antibodies directed towards NGF may be prepared according to standard methods. Monoclonal antibodies may be prepared according to general hybridoma methods of Kohler and Milstein, Nature (1975) 256:495-497), the trioma technique, the human B-cell hybridoma technique (Kozbor et al., Immunology Today (1983) 4:72) and the EBV-hybridoma technique (Cole et al., Monoclonal Antibodies And Cancer Therapy, pp. 77-96, Alan R. Liss, Inc., 1985).

Antibodies utilized in the present invention may be polyclonal antibodies, although monoclonal antibodies are preferred because they may be reproduced by cell culture or recombinantly, and may be modified to reduce their antigenicity. Polyclonal antibodies may be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, an NGF antigen comprising an antigenic portion of the NGF polypeptide is initially injected into any of a wide variety of mammals (e.g., mice, rats, rabbits, sheep or goats). Alternatively, in order to generate antibodies to relatively short peptide portions of NGF, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for NGF may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, preferably primed with pristine, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Antibodies that are immunologically specific to NGF, or specific epitopes thereof, may be utilized to quantify the protein utilizing techniques such as western blotting and ELISA, or to immuno-precipitate NGF from a sample containing a mixture of proteins and other biological materials. The methods and kits of the present invention are further suitable for use with surface-enhanced laser desorption ionization-time of flight (SELDI-TOF), which is another proteomic technology involved in quantitative analysis of protein mixtures. This technique utilizes stainless steel or aluminum-based supports, or chips, engineered with chemical (hydrophilic, hydrophobic, pre-activated, normal-phase, immobilized metal affinity, and cationic or anionic) or biological (antibody, antigen binding fragments (e.g. scFv), DNA, enzyme, or receptor) bait surfaces of 1-2 mm in diameter. These varied chemical and biochemical surfaces allow differential capture of proteins based on the intrinsic properties of the proteins themselves. Solubilized tissue or body fluids in volumes as small as 0.1 µl are directly applied to these surfaces, where proteins with affinities to the bait surface will bind. Following a series of washes to remove non-specifically or weakly bound proteins, the bound proteins are laser desorbed and ionized for mass spectrophotometric analysis. SELDI-TOF technology can further be coupled with tandem mass spectrometers for protein identification.

While immunoassays are preferred embodiments of the present invention due to their ease of use, other techniques for the detection and measurement of serum and/or plasma NGF levels are within the scope of the present invention.

Serum or plasma levels of NGF predictive of an occurrence of arrhythmia may be determined with reference to the normal baseline NGF levels in a patient and/or patient population. For example, a 2.5-fold or greater increase in serum or plasma NGF may be used as predictive of an occurrence of arrhythmia. Upon detection of an increase in serum NGF levels, the patient or physician may then take precautionary or therapeutic measures to avoid or reduce the likelihood of an impending cardiac arrhythmia or other diseased condition of the heart. The physician can then administer suitable therapeutic drugs or adjust the drug dosage for patients already receiving therapy and thus prevent arrhythmia, ischemia or sudden death. Suitable therapy for use in connection with the methods and systems are known in the art and may include any one or a combination of the following: delivering one or more pharmacological agents; stimulating myocardial hyperinnervation in the sinus node and right ventricle of the heart of the patient; and cardiac pacing, cardioversion, or defibrillation shocks. Pharmacologic therapeutic agents may include those which are known to exert an anti-arrhythmic effect, such as sodium channel blockers, β-blockers, potassium channel blockers, such as amiodarone and solatol, and calcium channel blockers, such as verapamil and diltiazem.

Other suitable anti-arrhythmic pharmacologic agents include anti-convulsant agents, such as phenytoin, carbamazepine, valproate, and phenobarbitone. Anti-convulsants work by selectively suppressing high frequency neuronal discharges in the central and peripheral nervous system. Anti-convulsants are also known to suppress cardiac sympathetic nerve discharges. Because of the importance of the autonomic nervous system in arrhythmogenesis, drugs that prevent the release of adrenergic neurotransmitters may thereby decrease the sympathetic outflow are useful for controlling cardiac arrhythmia.

It has been shown, for example, that phenytoin can also be used to suppress cardiac arrhythmia induced by digitalis toxicity. The action of phenytoin is related to use- and frequency-dependent selective suppression of high-frequency neuronal activity. The molecular mechanism for this is a voltage-dependent blockade of membrane sodium channels responsible for the action potential. Through this action, phenytoin obstructs the positive feedback that underlies the development of maximal seizure activity.

Anti-convulsants may block the sympathetic nerve discharges through two actions. One is frequency-dependent block of sodium currents and the second is a block of calcium currents. A combined channel blockade may account for the effects of anticonvulsant drugs. In addition to epilepsy, anti-convulsants, such as phenytoin and carbamazepine, are also useful in treating neuropathic pain, which is characterized by abnormal spontaneous and increased evoked activity from damaged areas of the peripheral nervous system.

Other suitable pharmacologic agents may also be used for the treatment of myocardial ischemia and may include, but are not limited to, statins, angiotensin-converting enzyme (ACE) inhibitors, aspirin, beta blockers, calcium channel blockers, and nitrates.

The methods and kits described herein are merely illustrative of the principles of the invention which may be implemented in alternative embodiments to achieve other ends than those specifically described herein. Accordingly, the following examples are set forth for the purpose of illustration only and are not construed as limitations on the methods and kits disclosed herein.

EXAMPLES

Example 1

Plasma Nerve Growth Factor Concentrations and the Recurrence of Atrial Fibrillation After Catheter Ablation Previous reports have indicated that radiofrequency catheter ablation (RFCA) in humans is associated with a significantly increased plasma nerve growth factor (NGF) concentration. Whether or not the magnitude of NGF increase is predictive of post-ablation atrial fibrillation (AF) recurrence is not clear. 17 patients who underwent RFCA for (AF) (N=15), or with atrial flutter (N=2) were studied. The latter 2 patients also had AF before procedure. The mean age was 51±8.8 years and 12 patients were men. The procedure time was 308±58 min for AF ablation, which included Lasso guided 4 pulmonary vein (PV) ostial ablation and creating cavotricupid isthmus block. The procedure times were 165±63 min for atrial flutter ablation, which included cavotricuspid isthmus block only. Average RF application was 73.5±15.2 min for AF and 52.9±47 min for atrial flutter. The patients were followed up for 11±1 months during which 6 patients had recurrent AF (N=5) or atrial flutter (N=1). In 2 of the 6 patients, the AF was transient. The remaining 11 patients had no recurrence of arrhythmia. The 6 patients with AF recurrence had NGF increased from 7.36±3.01 ng/ml (immediately after ablation) to 36.60±26.63 ng/ml in postoperative day (POD) 1 and 30.01±19.81 ng/ml in POD 2. The average increase was 5.05±3.75 fold (range 1.77 to 11.83) in POD 1. In contrast, the 11 patients without AF recurrence had NGF increased from 17.21±12.93 ng/ml (immediately post-ablation) to 26.43±17.60 ng/ml in POD 1. The average increase was 1.79±0.57 fold (range 0.88-2.53, P=0.039 compared with patients with recurrence) in POD1. Among the 6 patients with recurrent AF or flutter, 4 had an NGF increase of >2.53 fold. Therefore, a NGF increase of >2.53 fold in POD1 is associated with 67% probability of post-ablation arrhythmia recurrence. On the other hand, if the NGF increase is ≦2.53 fold, there is an 85% (11/13) probability that the patient will be arrhythmia-free during follow up. Thus, it was found that there was a significant association between the magnitude of NGF increase and the post-ablation AF recurrence in patients undergoing radiofrequency catheter ablation.

Example 2

Elevation of Aortic and Coronary Artery Nerve Growth Factor following Acute Myocardial Infarction in Humans In a canine model, acute myocardial infarction (AMI) results in an upregulation of nerve growth factor (NGF) expression in the myocardium with peak activity at 1 week after MI. The total blood NGF rapidly increased after AMI, and stayed high for at least one month. The increased NGF was associated with cardiac nerve sprouting, which contributes to arrhythmogenesis after MI. It was hypothesized that human patients with AMI might show similar increases in NGF levels with its resulting consequences.

Methods. Blood was drawn simultaneously from aorta and culprit coronary artery in ten AMI (acute myocardial infarction) patients undergoing urgent cardiac catheterization. Serum NGF concentrations was quantified by using enzyme-linked immunosorbant assay. In each patient the time between blood sampling and the onset of chest discomfort was recorded Results: There were 9 males and 1 female. The mean age was 63 yrs (range 42 to 82). There was no significant difference between the aortic and coronary arterial NGF levels in each patient. Patients with AMI>6 hours had significantly higher aortic (235±131 ng/ml) and coronary artery (225±128 ng/ml) NGF levels than patients with AMI<6 hours (58±71 ng/ml and 53±131 ng/ml, respectively, p=0.036 for both comparisons). The large standard deviation indicates a large individual variation of the NGF concentration. There is a good linear correlation between the time since the onset of chest pain and the NGF levels in the aorta (r=0.80, p=0.0057) and in the coronary artery (r=0.81, p=0.0048). One patient with a highly elevated NGF level (447 ng/ml) developed ventricular tachycardia nine months later, documented by an implantable cardioverter-defibrillator.

CONCLUSION

There is a time-dependent increase in systemic NGF concentrations in AMI patients. Increased NGF concentrations following AMI may cause increased cardiac nerve sprouting, resulting in an increases risk for serious ventricular arrhythmias.

What is claimed is:

1. A method for determining an increased likelihood of the occurrence of a human cardiac arrhythmia, myocardial ischemia, a congestive heart failure and other disease conditions of the human heart comprising:
   measuring the serum levels of nerve growth factor (NGF) in a human subject;
   comparing the measured NGF serum level with the normal NGF level to determine whether there is an increase in the serum NGF level; and
   determining that the human subject has the increased likelihood of the occurrence of the human cardiac arrhythmia, myocardial ischemia, the congestive heart failure and other disease conditions of the human heart when there is a 2.5-fold or greater increase in the serum NGF level, or
   determining that the human subject does not have an increased likelihood of the occurrence of a human cardiac arrhythmia, myocardial ischemia, a congestive heart failure and other disease conditions of the human heart when there is not the 2.5-fold or greater increase in scrum or plasma NGF level.

2. The method of claim 1 wherein the normal NGF level is about 10 ng/ml.

3. The method of claim 1, comprising determining that the human subject has the increased likelihood of the occurrence of the human cardiac arrhythmia, myocardial ischemia, the congestive heart failure and other disease conditions of the human heart when there is a 5.05-fold or greater increase in the serum NGF level.

4. The method of claim 1, comprising determining that the human subject has the increased likelihood of the occurrence of the human cardiac arrhythmia, myocardial ischemia, the congestive heart failure and other disease conditions of the human heart when there is a 8.80-fold or greater increase in scrum NGF level.

5. A method for determining an increased likelihood of the occurrence of a human cardiac arrhythmia, myocardial ischemia, a congestive heart failure and other disease conditions of the human heart comprising:
   measuring the serum levels of nerve growth factor (NGF) in a human subject;
   determining if the measured NGF serum level is greater than about 25 ng/ml; and
   determining that the human subject has an increased likelihood of the occurrence of the human cardiac arrhythmia, myocardial ischemia, the congestive heart failure and other disease conditions of the human heart when the measured NGF serum level is greater than 25 ng/ml, or
   determining that the human subject does not have the increased likelihood of the occurrence of the human cardiac arrhythmia, myocardial ischemia, the congestive heart failure and other disease conditions of the human heart when the measured NGF serum level is not greater than 25 ng/ml.

6. The method of claim 5, wherein the other disease conditions of the human heart is a myocardial infarction, and the method comprises determining that the human subject has the increased likelihood of the occurrence of the myocardial infarction when the serum NGF level is 104 ng/ml or greater.

7. The method of claim 5, wherein the other disease conditions of the human heart is a myocardial infarction, and the method comprises determining that the human subject has the increased likelihood of the occurrence of the myocardial infarction when the serum NGF level is 235 ng/ml or greater.

8. The method of claim 5, wherein the other disease conditions of the human heart is a myocardial infarction, and the method comprises determining that the human subject has the increased likelihood of the occurrence of the myocardial infarction when the serum NGF level is 366 ng/ml or greater.

9. The method of claim 5, wherein the other disease conditions of the human heart is a myocardial infarction, and the method comprises determining that the human subject has the increased likelihood of the occurrence of the myocardial infarction when the serum NGF level is 97 ng/ml or greater.

10. The method of claim 5, wherein the other disease conditions of the human heart is a myocardial infarction, and the, method comprises determining that the human subject has the increased likelihood of the occurrence of the myocardial infarction when the serum NGF level is 225 ng/ml or greater.

11. The method of claim 5, wherein the other disease conditions of the human heart is a myocardial infarction, and the method comprises determining that the human subject has the increased likelihood of the occurrence of the myocardial infarction when the scrum NGF level is 353 ng/ml or greater.

12. The method of claim 5, wherein the other disease conditions of the human heart is a myocardial infarction, and the method comprises determining that the human subject has the increased likelihood of the occurrence of the myocardial infarction when the serum NGF level is 447 ng/ml or greater.

13. A method for treating the occurrence of a human cardiac arrhythmia, myocardial ischemia, a congestive heart failure and other disease conditions of the human heart comprising:
    measuring the serum levels of nerve growth factor (NGF) in a human subject;
    comparing the measured NGF serum level with the normal NGF level of about 10 ng/ml;
    determining if the measured NGF serum level is greater than about 25 ng/ml;
    determining that the human subject has an increased likelihood of the occurrence of the human cardiac arrhythmia, myocardial ischemia, the congestive heart failure and other disease conditions of the human heart when the measured NGF serum level is greater than 25 ng/ml, or
    determining that the human subject does not have the increased likelihood of the occurrence of the human cardiac arrhythmia, myocardial ischemia, the congestive heart failure and other disease conditions of the human heart when the measured NGF serum level is not greater than 25 ng/ml; and
    administering suitable therapy if the human subject has the increased likelihood of the occurrence of the human cardiac arrhythmia, myocardial ischemia, the congestive heart failure and other disease conditions of the human heart.

14. The method of claim 13 wherein the therapy is delivering one or more pharmacological agents.

15. The method of claim 13 wherein the therapy is stimulating myocardial hyperinnervation in the sinus mode and right ventricle of the patient heart.

16. The method of claim 13 wherein the therapy is cardiac pacing.

17. The method of claim 13 wherein the therapy is cardioversion.

18. The method of claim 13 wherein the therapy is defibrillation shock to the patient heart.

19. The method of claim 14 wherein the pharmacological agents are further described as sodium channel blockers, β-blockers, potassium channel blockers, such as amiodarone and solatol, and calcium channel blockers, such as verapamil and diltiazem and phenytoin, carbamazepine, valproate, and phenobarbitone.

* * * * *